United States Patent
Suddaby

[11] Patent Number: 6,159,244
[45] Date of Patent: Dec. 12, 2000

[54] EXPANDABLE VARIABLE ANGLE INTERVERTEBRAL FUSION IMPLANT

[76] Inventor: Loubert Suddaby, 76 Tanglewood Dr., Orchard Park, N.Y. 14127

[21] Appl. No.: 09/365,223

[22] Filed: Jul. 30, 1999

[51] Int. Cl.[7] .................................................. A61F 2/44
[52] U.S. Cl. .......................................... 623/17.11; 606/61
[58] Field of Search ........................... 623/17.11, 17.13, 623/17.15, 17.16; 606/53, 60, 61, 63, 73; 411/55, 18, 21, 35, 298, 413

[56] References Cited

U.S. PATENT DOCUMENTS

| | | | |
|---|---|---|---|
| 925,006 | 6/1909 | Mason | 411/25 |
| 5,026,373 | 6/1991 | Rsy et al. | 606/61 |
| 5,505,732 | 4/1996 | Michelson . | |
| 5,653,762 | 8/1997 | Pisharodi . | |
| 5,665,122 | 9/1997 | Kambin . | |
| 5,683,463 | 11/1997 | Godefroy et al. . | |
| 5,865,848 | 2/1999 | Baker | 623/17 |
| 5,876,457 | 3/1999 | Picha et al. | 623/17 |
| 5,888,228 | 3/1999 | Knotche et al. | 623/17 |
| 5,980,522 | 11/1999 | Koros et al. | 606/61 |
| 6,045,579 | 4/2000 | Hochshuler et al. | 623/17 |

Primary Examiner—Pedro Philogene
Attorney, Agent, or Firm—Shoemaker and Mattare

[57] ABSTRACT

An expandable intervertebral fusion implant includes a pair of semi-cylindrical shells having mating surfaces which resist shifting when the parts are assembled. The shells have pillars provided with teeth which permit the shells to be ratcheted outward after they have been placed between spinal elements. The pillars are curved, or extend from their shells at a non-perpendicular angle, so that the resulting implant is tapered, to accommodate non-parallel spinal element end plates and thus maintain proper spinal curvature.

8 Claims, 6 Drawing Sheets

EXPANDABLE VARIABLE ANGLE INTERVERTEBRAL FUSION IMPLANT

BACKGROUND OF THE INVENTION

This invention relates to an intervertebral fusion implant. The class of implements to which this invention pertains serve to stabilize adjacent vertebral elements, thereby facilitating the development of a bony union between them and thus long term spinal stability.

Of all animals possessing a backbone, human beings are the only creatures who remain upright for significant periods of time. From an evolutionary standpoint, this erect posture has conferred a number of strategic benefits, not the least of which is freeing the upper limbs for purposes other than locomotion. From an anthropologic standpoint, it is also evident that this unique evolutionary adaptation is a relatively recent change, and as such has not benefitted from natural selection as much as have backbones held in a horizontal attitude. As a result, the stresses acting upon the human backbone (or "vertebral column"), are unique in many senses, and result in a variety of problems or disease states that are peculiar to the human species.

The human vertebral column is essentially a tower of bones held upright by fibrous bands called ligaments and contractile elements called muscles. There are seven bones in the neck or cervical region, twelve in the chest or thoracic region, and five in the low back or lumbar region. There are also five bones in the pelvic or sacral region which are normally fused together and form the back part of the pelvis. This column of bones is critical for protecting the delicate spinal cord and nerves, and for providing structural support for the entire body.

Between the vertebral bones themselves exist soft tissue structures—discs—composed of fibrous tissue and cartilage which are compressible and act as shock absorbers for sudden downward forces on the upright column. The discs allow the bones to move independently of each other, as well. The repetitive forces which act on these intervertebral discs during repetitive day-to-day activities of bending, lifting and twisting cause them to break down or degenerate over time.

Presumably because of humans' upright posture, their intervertebral discs have a high propensity to degenerate. Overt trauma, or covert trauma occurring in the course of repetitive activities disproportionately affect the more highly mobile areas cf the spine. Disruption of a disc's internal architecture leads to bulging, herniation or protrusion of pieces of the disc and eventual disc space collapse. Resulting mechanical and even chemical irritation of surrounding neural elements (spinal cord and nerves) cause pain, attended by varying degrees of disability.

In addition, loss of disc space height relaxes tension on the longitudinal spinal ligaments, thereby contributing to varying degrees of spinal instability such is spinal curvature.

The time-honored method of addressing the issues of neural irritation and instability resulting from severe disc damage have largely focused on removal of the damaged disc and fusing the adjacent vertebral elements together. Removal of the disc relieves the mechanical and chemical irritation of neural elements, while osseous union (bone knitting) solves the problem of instability.

While cancerous bone appears ideal to provide the biologic components necessary for osseous union to occur, it does not initially have the strength to resist the tremendous forces that may occur in the intervertebral disc space, nor does it have the capacity to adequately stabilize the spine until long term bony union occurs. For these reasons, may spinal surgeons have found that interbody fusion using bone alone has an unacceptably high rate of bone graft migration or even expulsion or nonunion due to structural failures of the bone or residual degrees of motion that retard or prohibit bony union. Intervertebral prostheses in various forms have therefore been used to provide immediate stability and to protect and preserve an environment that fosters growth of grafted bone such that a structurally significant bony fusion can occur.

U.S. Pat. No. 5,505,732, U.S. Pat. No. 5,653,762, U.S. Pat. No. 5,665,122, and U.S. Pat. No. 5,683,463 describe different prior spinal implants. The implant shown in U.S. Pat. No. 5,483,463 is hollow and tubular, with communicating windows in the top and bottom surfaces. External ribs, which may be serrated, stabilize the implant once it is inserted between the vertebrae. In U.S. Pat. No. 5,665,122, an intervertebral cage is rendered expandable by a wedging mechanism. The degree of expansion is rather limited, however. U.S. Pat. Nos. 5,653,762 and U.S. Pat. No. 5,505,732 show shaft-type tools used for installing implants. The prior devices do not enable one to achieve great ranges of implant height, or to adjust taper angle for kyphotic and lordotic situations.

Limitations of most present-day intervertebral implants ire significant and revolve largely around the marked variation in disc space shape and height that results from either biologic variability or pathologic change. For example, if a disc space is 20 mm in height, a circular implant bridging this gap requires a minimum diameter of 20 mm just to contact the end plate of the vertebral bone. Generally, end plate disruption must occur to allow a generous bony union, meaning that an additional 2–3 mm must be added on either end, resulting in a final implant size of 24–26 mm. During implantation from an anterior approach (from the front of the body), excessive retraction (pulling) is often required on the great blood vessels which greatly enhances the risk of devastating complications such as vascular tears or thrombosis. On the other hand, during a posterior approach, large implant diameters may require excessive traction on neural elements for adequate placement, even if all posterior bony elements are removed. In some instances, an adequate implant size cannot be inserted posteriorly, particularly if there is a significant degree of ligamentous laxity requiring higher degrees of distraction to obtain stability by tautening the annular ligamentous tension band. Compromising on implant size risks sub-optimal stability or a loose implant, which has a greater chance for migration within or expulsion from the disc space. The alternative of excessively retracting neural elements to facilitate a posterior implant application results in a neuropraxia at best and permanent neural damage at worst.

SUMMARY OF THE INVENTION

It is the object of this invention to provide an expandable intervertebral fusion implant that is both simple to manufacture and simple to use in daily clinical surgical practice while remaining versatile enough to address the complex biologic and pathologic variability of the human spine.

It is also intended that this device be applicable to all generally accepted surgical approaches to the spine, including microsurgical and endoscopic applications.

To achieve these objectives, a pair of metal shells are distracted inside an intervertebral space that has been appropriately prepared for fusion. An expansible installation tool is used to achieve optimal distraction, and the shells are held apart by teeth on pillars which extend from semicylindrical bases. These pillars preferably are curved to facilitate differential expansion of one end of the implant relative to the other to account for normal variations in the angle of the adjacent end plates; i.e., to preserve or enhance the lordotic or kyphotic attitude of adjacent vertebral body elements that are to be fused. The installation tool is then unscrewed and disengaged, leaving the component parts as a stable assembly that can be packed with bone to promote osseous union.

The present invention not only provides an expandable intervertebral fusion implant, but also lends itself readily to use in anterior, lateral and posterior approaches. In addition, one can insert devices of different sizes or angulations in a single intervertebral space to address lateral differences in disc space height to account for degrees of scoliosis, lordosis or kyphosis.

The tubular implant approximates a cylinder that is larger at one end and divided into cranial (upper) and caudal (lower) shells that contact the end plates of the vertebral bones above and below and can be distracted, or spread apart, by a screw-type installation tool until optimal distraction of the vertebral elements and appropriate tension on the ligamentous structures is achieved.

The larger end has larger corrugations relative to the smaller end and therefore has the potential to expand to a greater height to address needs for greater kyphosis or lordosis at a single interspace. By varying the ratio of heigh of the larger corrugations to the smaller ones, varying degrees of angulation can be accommodated. The installation tool is then retracted, allowing the two components to seat against one another and lock together, and the tool is then removed. The implant assembly is now packed with auto graft or auto graft bone to allow long term bony union to develop betwnn the vertebral elements. A cap is then placed over the anterior surface to hold the bone in place and to prevent lateral shifting of the upper and lower shells. Lateral shifting of the components is also prevented by "tongue and groove" faces on the contacting surface of adjacent corrugations.

The advantages provided by this invention include (1) the fact that both the tool and the implant components are of simple manufacture and (2) because of its expandable nature, this implant has the potential for use in microsurgical laminotomy, where only a small opening is made in the spine, resulting in minimal retraction of neural structures and maximizing preservation of posterior bony and ligaments spinal elements, and (3) lordotic and kyphotic orientations in the spine can be addressed. Most existing posterior interbody approaches require extensive bone removal to achieve spinal fusion whether or not an implant is used.

BRIEF DESCRIPTION OF THE DRAWINGS

In the accompanying drawings.

DESCRIPTION OF THE PREFERRED EMBODIMENT

Figure 1:
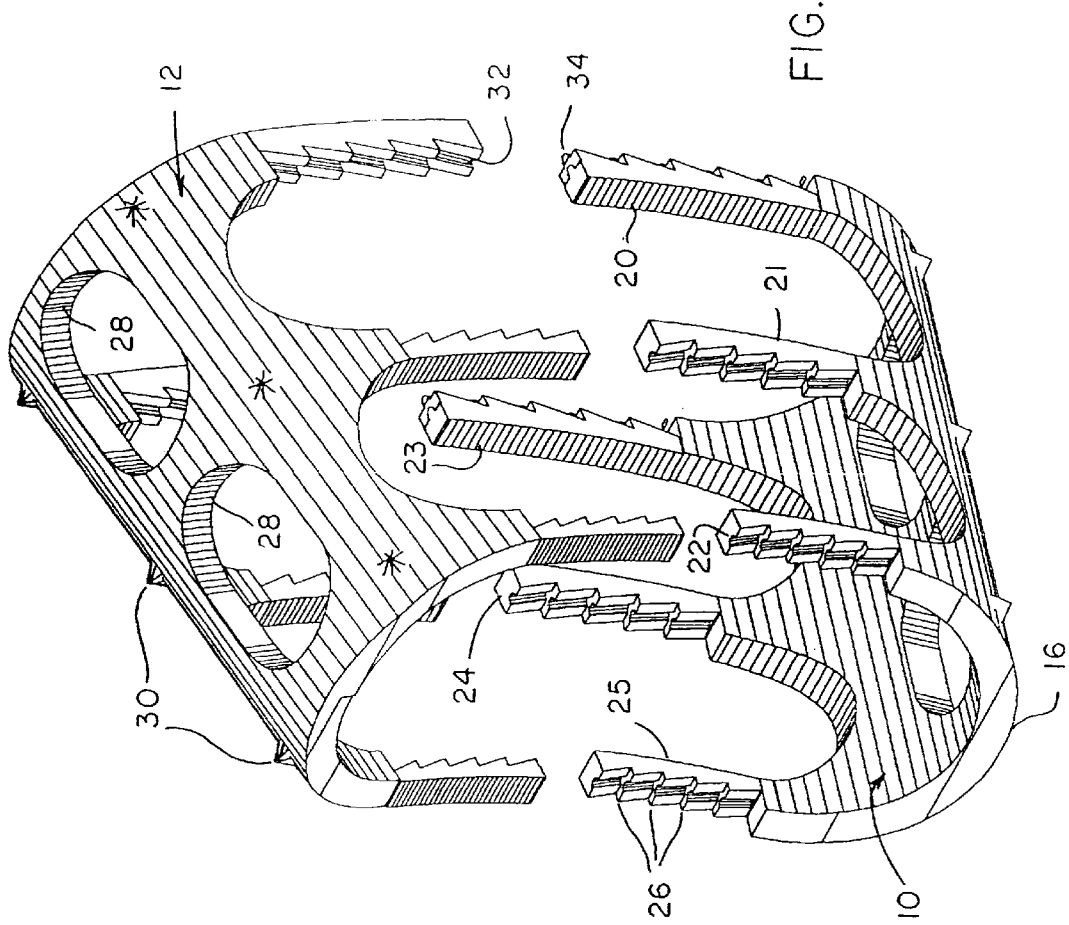
FIG. 1 is an exploded perspective view of a pair of shells forming an implant according to the invention.
Figure 2:
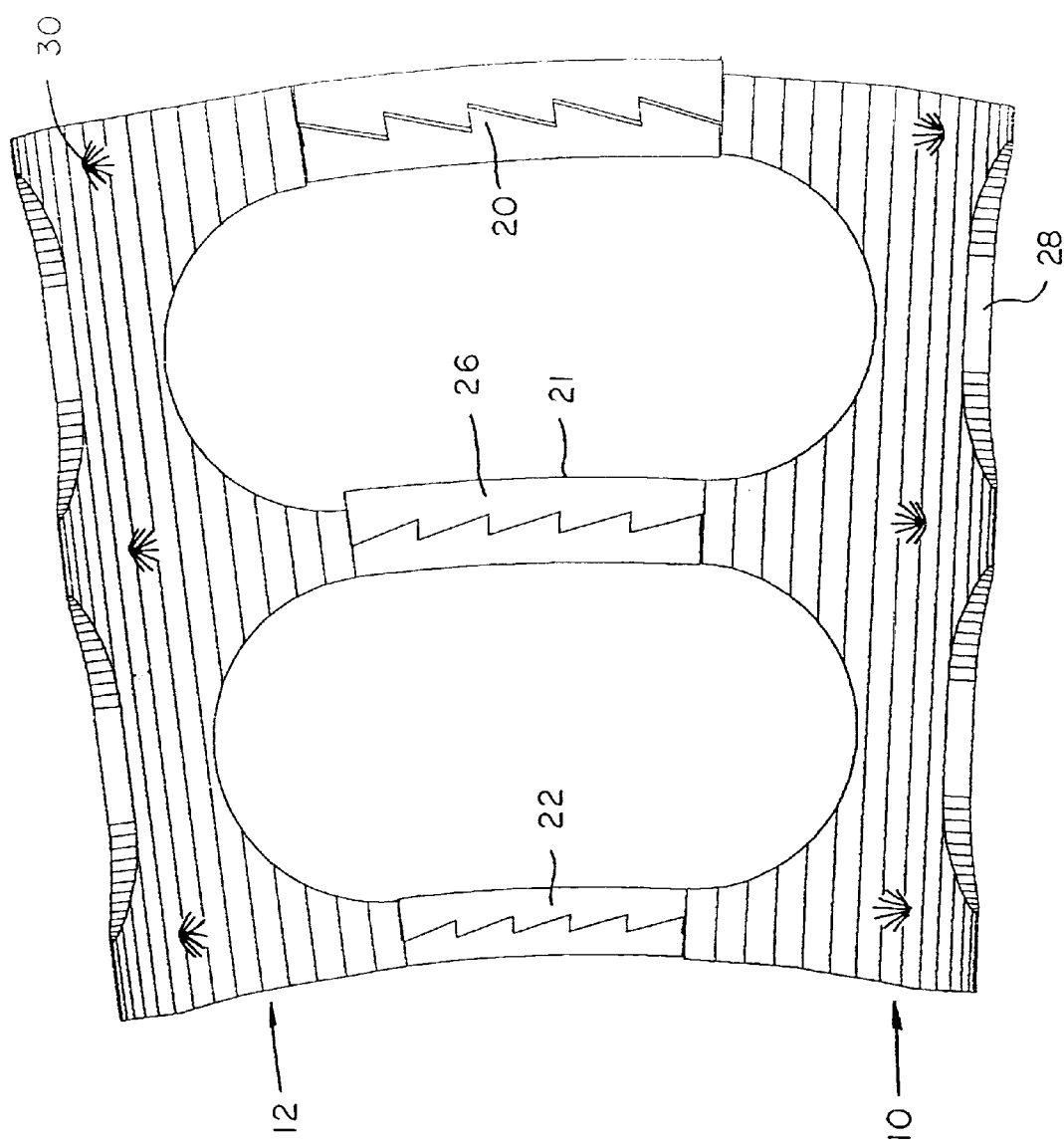
FIG. 2 is a side elevation, showing the shells assembled in a collapsed configuration.
Figure 3:
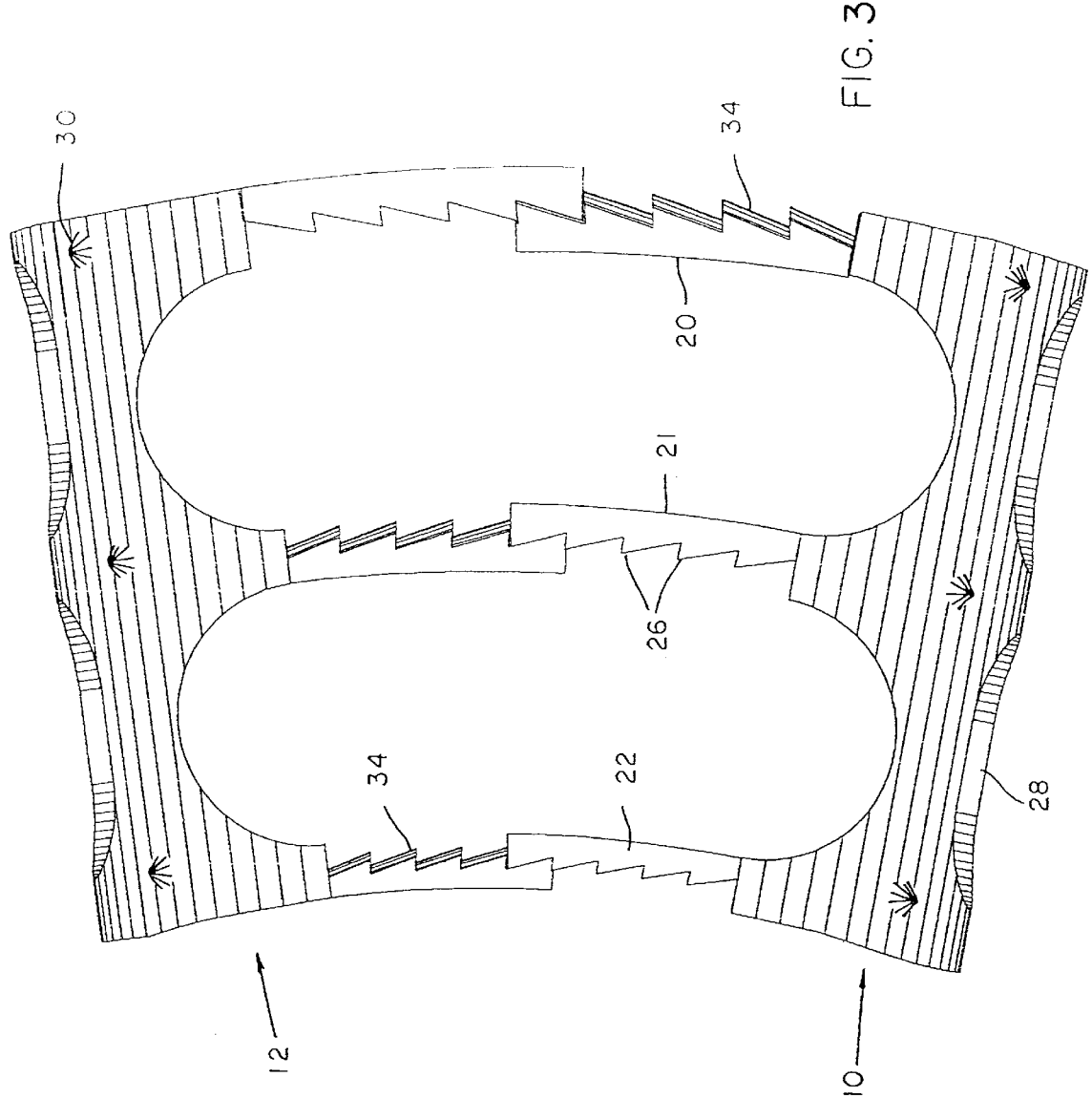
FIG. 3 is a view like FIG. 2, showing the shells expanded between adjacent vertebral elements.

An expandable intervertebral fusion implant embodying the invention appears in FIGS. 1–3. The implant comprises a pair of mating metal shells 10, 12. Each shell has a semicylindrical base 16 and an array of pillars 20,21,22,23, 24,25 extending parallel to one another from the lateral edges 18 of the base.

In the preferred form of the invention, each of the pillars is curved, following the circumference of an imaginary cylinder having an axis "A" extending along the line of intersection between the planes forming the lateral edges of the two shells. Each pillar has a generally rectangular cross-section. Three sides of the pillar are smooth, while a fourth is serrated, having a plurality of triangular teeth 26 raked in one direction to as to permit only expansion of the shells after they have been assembled initially in a retracted position.

The teeth on the endmost pillars 20,22,23,25 face in opposite longitudinal directions, so that when the shells are assembled, no relative longitudinal movement is possible, and the shells can move away from one another only when sufficient expanding force is applied to bend the pillars slightly, allowing the interfering teeth to pass over one another. During expansion, each time the tips of the teeth clear, the pillars snap back to their rest positions; this ratcheting action prevents the implant from collapsing, and also may provide useful tactile or audible feedback to the surgeon.

In the preferred form of the invention, the pitch (spacing) of the teeth on each pillar is proportional to its distance from the axis "A", that is, the more distant teeth have a greater pitch. This permits each incremental expansion of the shells to follow an arc about the axis "A", so that the taper angle of the implant grows as the implant is expanded.

Figure 4:
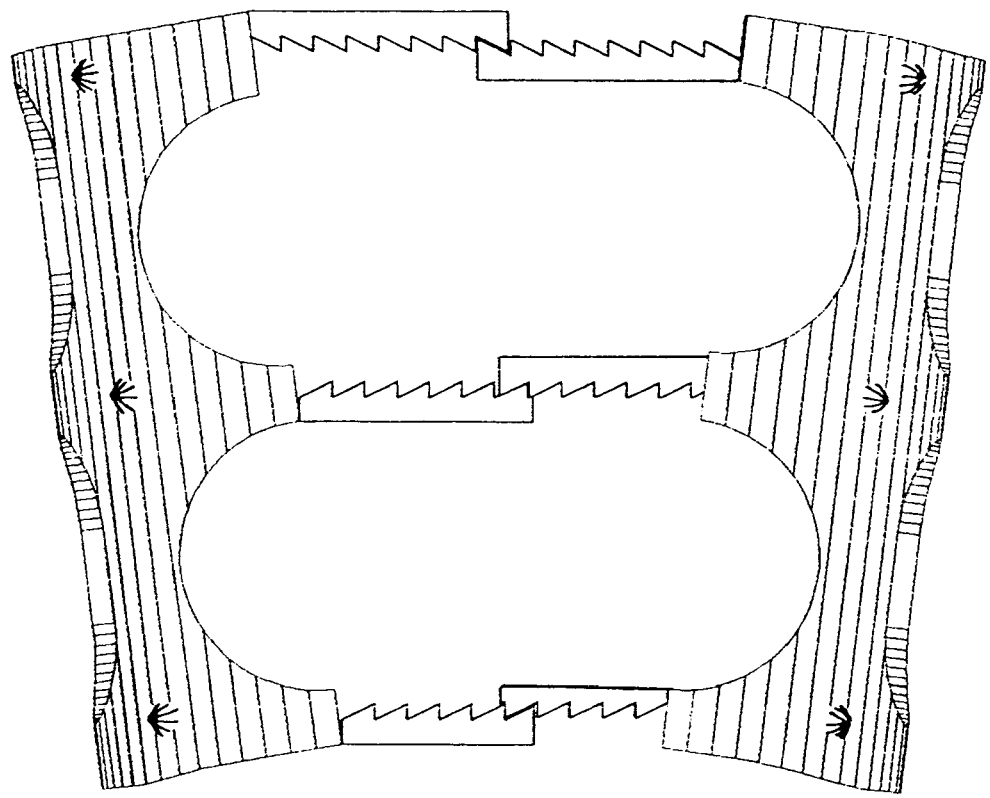
FIG. 4 is a view like FIG. 2, showing an alternative embodiment of the invention.

Alternatively (FIG. 4), the pillars can be straight and parallel, with all the teeth having the same pitch, so that the relative movement of the shells during expansion is purely translational, and the taper angle of the implant remains constant, according to the angle at which the pillars extend from the longitudinal edges of the shell. Other geometries may prove useful as well. One could extend the principles of the invention to produce a device whose taper angle actually decreases during expansion, for example.

Each shell preferably has one or two windows 28 to encourage bone growth. The points 30 positioned around the windows dig into the surfaces of the bones between which the implant is installed.

Figure 5:
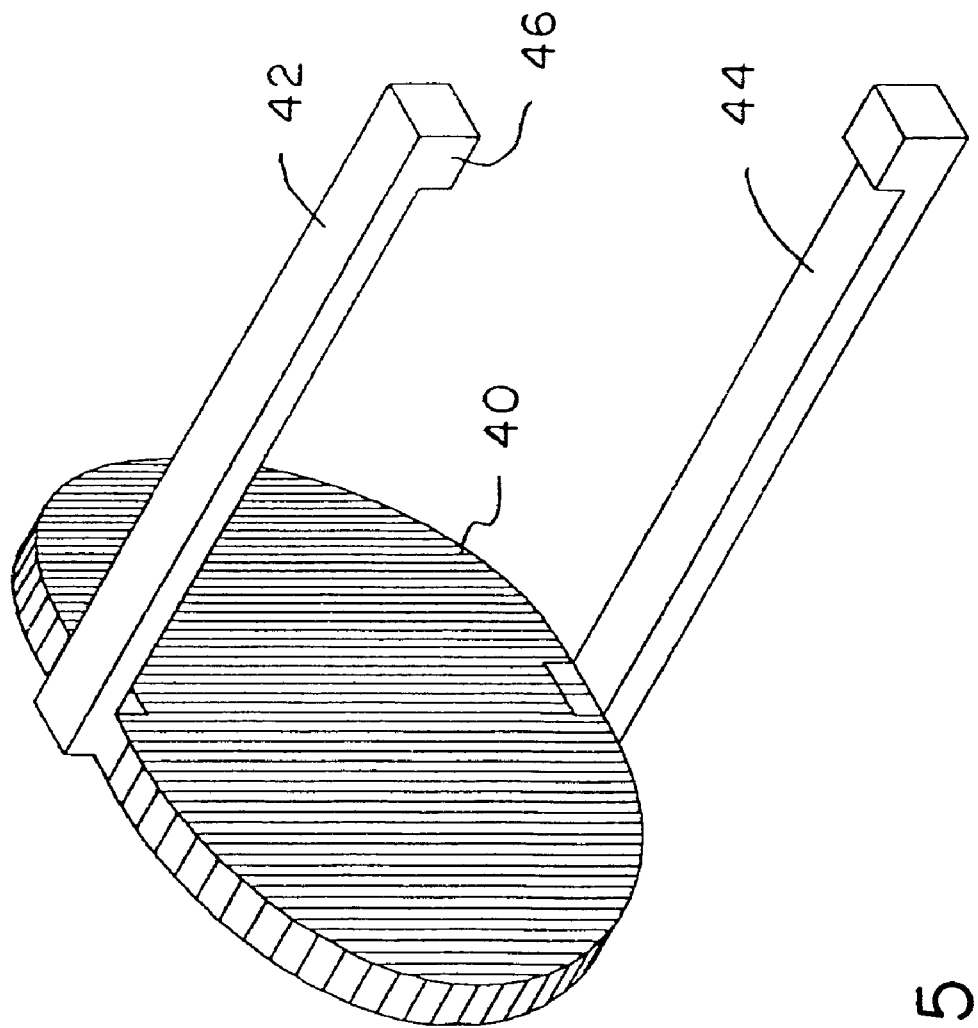
FIG. 5 is a perspective view of an anterior end cap shown in FIG. 1.
Figure 6:
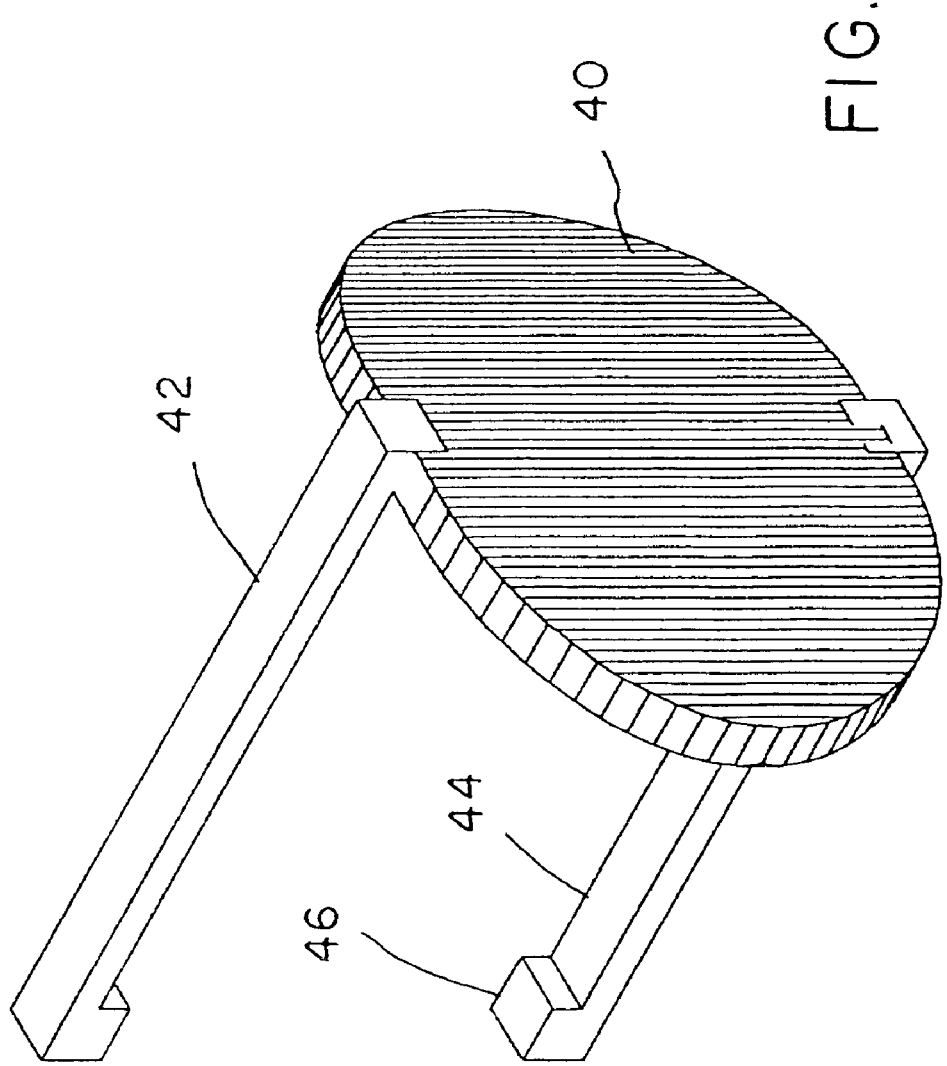
FIG. 6 is a similar view of a posterior endcap.

The shells form an open-ended structure. It may be desired to close one or both ends. If so, an end cap may be applied over an open end. Preferred end caps, include a oval plate 40 having slight outward concavity (FIG. 5) or convexity (FIG. 6) corresponding to the shapes of the ends of the implant. The cap is retained on the implant by a pair of arms 42,44, each of which has a hook 46 or the like at its free end, for engaging over the far end of the implant. Grooves or other structure, not shown, may be provided on the implant surfaces to retain the caps more securely.

The shells are provided with complementary structures such as detents 32 and ribs 34 on opposing teeth, to keep the shells from moving sideways once the spacer has been installed The shells and the caps may be made of the same material, or different materials. Suitable materials include stainless steel, titanium, ceramic, graphite, and various plastics and composites of the foregoing. The selection of material may affect the dimensions or proportions of the parts somewhat, but is generally a matter of design choice.

To install an implant, the shells, preassembled in their fully collapsed configuration, are placed in the selected empty intervertebral space by means of an expandable tool (not shown), with its jaws retracted. Then the jaws are spread apart, forcing the shells outward into contact with the bones above and below. The points 30 on the shells dig into the bony material somewhat. Once the jaws are retracted, the tool can be removed from the site, and the implant remains expanded.

It may be appreciated that changes in geometry and the like may be made to the elements of the invention while retaining their essential function. For example, the bases of the shells might be frustoconical, rather than cylindrical, and the number of pillars on either side of each shell could be any plural number.

Since the invention is subject to modifications and variations, it is intended that the foregoing description and the accompanying drawings shall be interpreted as only illustrative of the invention defined by the following claims.

I claim:

1. An expandable intervertebral fusion implant comprising a pair of shells, each having a generally semicylindrical base having lateral edges and a plurality of pillar projecting from each of the lateral edges, at least some of the pillars on one shell having ratchet teeth adapted to engage complementary ratchet teeth on the other shell, the teeth preventing the shells from moving toward one another, but permitting the shells to move away from one another as the pillars deflect when the shells are driven apart with sufficient force.

2. The invention of claim 1, wherein the pillars are non-perpendicular to the axes of their bases, so that the implant when assembled tapers from one end to the other.

3. The invention of claim 1, wherein the pillars are curved about a remote axis and have teeth whose pitch varies proportionately with the distance of the teeth from said axis, so that the shells have arcuate relative motion as they are expanded, and the taper angle of the implant increases during expansion.

4. The invention of claim 1, wherein each of said bases has at least one aperture for facilitating bone growth around the implant.

5. The invention of claim 1, wherein each of said bases has at least one point for engaging an end plate of a vertebral element to stabilize the position of the implant.

6. The invention of claim 1, further comprising an end cap for covering one open end of the implant, said end cap comprising a plate and a pair of retaining arms extending from opposite sides of the plate, each of said arms having means for engaging in opposite end of the implant.

7. The invention of claim 6, wherein the end plate is convex.

8. The invention of claim 6, wherein the end plate is concave.

* * * * *